US008922916B2

(12) United States Patent
Yamamoto et al.

(10) Patent No.: US 8,922,916 B2
(45) Date of Patent: Dec. 30, 2014

(54) ENDOSCOPE OBJECTIVE LENS AND ENDOSCOPE

(71) Applicant: FUJIFILM Corporation, Tokyo (JP)

(72) Inventors: Chikara Yamamoto, Saitama-ken (JP); Yoshiaki Ishii, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/270,728

(22) Filed: May 6, 2014

(65) Prior Publication Data

US 2014/0240855 A1 Aug. 28, 2014

Related U.S. Application Data

(63) Continuation of application No. PCT/JP2012/007125, filed on Nov. 7, 2012.

(30) Foreign Application Priority Data

Nov. 9, 2011 (JP) .................................. 2011-245363

(51) Int. Cl.
*G02B 23/24* (2006.01)
*A61B 1/00* (2006.01)
*G02B 13/04* (2006.01)
*A61B 1/005* (2006.01)

(52) U.S. Cl.
CPC .......... *G02B 23/243* (2013.01); *A61B 1/00188* (2013.01); *G02B 13/04* (2013.01); *A61B 1/0051* (2013.01)
USPC .......................................... 359/782; 359/781

(58) Field of Classification Search
CPC ... G02B 23/243; G02B 13/04; A61B 1/00188
USPC .................................................... 359/781, 782
See application file for complete search history.

(56) References Cited

U.S. PATENT DOCUMENTS

| | | | |
|---|---|---|---|
| 5,390,048 | A | 2/1995 | Miyatake et al. |
| 5,539,579 | A | 7/1996 | Miyatake et al. |
| 6,353,504 | B1 | 3/2002 | Yamamoto |
| 7,982,975 | B2 | 7/2011 | Takato |
| 2014/0218811 | A1* | 8/2014 | Yamamoto .................... 359/749 |

FOREIGN PATENT DOCUMENTS

| | | |
|---|---|---|
| JP | 05-150159 | 6/1993 |
| JP | 2876252 | 3/1999 |
| JP | 2001-091832 | 4/2001 |
| JP | 2004-021158 | 1/2004 |
| JP | 2009-198855 | 9/2009 |
| JP | 2009-294496 | 12/2009 |

OTHER PUBLICATIONS

International Search Report, PCT/JP2012/007125, Feb. 19, 2013.

* cited by examiner

*Primary Examiner* — David N Spector
(74) *Attorney, Agent, or Firm* — Young & Thompson

(57) ABSTRACT

An endoscope objective lens substantially consists of four lens groups consisting of, in order from the object side, a negative first lens group, a positive second lens group, a negative third lens group and a positive fourth lens group. During focusing from the farthest object to the nearest object, the first lens group is fixed, and the second lens group and the third lens group are moved along the optical axis. The third lens group includes a cemented lens that is formed by a positive lens and a negative lens cemented together in this order from the object side, and the cemented surface of the cemented lens is oriented such that the concave surface faces the object side.

15 Claims, 10 Drawing Sheets

ENDOSCOPE OBJECTIVE LENS AND ENDOSCOPE

TECHNICAL FIELD

The present invention relates to an endoscope objective lens and an endoscope, and more particularly to an endoscope objective lens where focusing from the farthest object to the nearest object is achieved by moving part of lens groups in the system, and an endoscope provided with the endoscope objective lens.

BACKGROUND ART

There are demands for endoscopes that allows the user to perform general observation of a wide range and detailed local observation of an affected area, or the like, which is found during the general observation. Conventionally, such demands have often been met by using a fixed focus lens with deep depth of field. However, further improvement of image quality is now desired, since there are trends of endoscopes with higher pixel density and wider angle of view, or analysis or observation is performed using images captured with an endoscope.

Considering the above-described situation, endoscope objective lenses that can be changed between a far point side observation state (WIDE) suitable for general observation and a near point magnified observation state (TELE) suitable for local observation depending on the situation of use of the endoscope are now being used. As prior art examples thereof, objective lenses disclosed in Japanese Patent No. 2876252 and Japanese Unexamined Patent Publication Nos. 2001-091832 and 2009-294496 (hereinafter, Patent Documents 1, 2 and 3, respectively) for example, are known.

Patent Document 1 discloses an objective lens having a four-group configuration with a negative-positive-negative-positive refractive power arrangement, wherein the above-described change of the state is achieved by moving only the third group. Patent Document 2 discloses an objective lens having a four-group configuration with a negative-positive-negative-positive refractive power arrangement, wherein the above-described change of the state is achieved by moving the third lens group and one of the second and fourth lens groups. Patent Document 3 discloses an objective lens having a three-group configuration with a positive-negative-positive refractive power arrangement, wherein the above-described change of the state is achieved by moving only the second group.

DISCLOSURE OF INVENTION

In the prior art examples disclosed in Patent Documents 1 and 2, each lens group to be moved is formed by a single lens in most cases. With such a lens system, variation of aberration, in particular, variation of chromatic aberration along with movement of the lens or lenses cannot be sufficiently corrected. As to chromatic aberration correction of a lens system in the above-described field, influence of a negative lens group, among the lens group(s) to be moved, is large. In order to minimize the variation of chromatic aberration along with movement of the lens, it is preferable that the lens to be moved is a cemented lens. In view of these circumstances, a configuration where the negative lens group to be moved is formed by a cemented lens is conceivable.

In Example 8 in Patent Document 1 and Example 3 in Patent Document 3, a cemented lens formed by a positive lens and a negative lens that are cemented together in this order from the object side is used as the negative lens group to be moved. However, in these cases, only one lens group is moved, and variation of the chromatic aberration along with movement of the lens cannot be sufficiently corrected.

In view of the above-described circumstances, the present invention is directed to providing an endoscope objective lens that can provide a magnified observation effect and has successfully corrected aberrations with low variation of aberration, in particular, low variation of chromatic aberration, and an endoscope provided with the endoscope objective lens.

The endoscope objective lens of the invention substantially consists of four lens groups, the four lens groups consisting of, in order from the object side, a first lens group having a negative refractive power, a second lens group having a positive refractive power, a third lens group having a negative refractive power, and a fourth lens group having a positive refractive power, wherein, during focusing from a farthest object to a nearest object, the first lens group is fixed, and the second lens group and the third lens group are moved along an optical axis, and the third lens group consists of a cemented lens that is formed by a positive lens and a negative lens cemented together in this order from an object side, wherein a cemented surface of the cemented lens is oriented such that a concave surface faces the object side.

In the endoscope objective lens of the invention, it is preferable that the conditional expression (1) below is satisfied, it is more preferable that the conditional expression (1A) below is satisfied, or it is even more preferable that the conditional expression (1B) below is satisfied:

$$0 < \nu n - \nu p \tag{1}$$

$$3 < \nu n - \nu p \tag{1A) or}$$

$$5 < \nu n - \nu p \tag{1B}$$

where $\nu n$ is an Abbe number with respect to the d-line of the negative lens forming the cemented lens, and $\nu p$ is an Abbe number with respect to the d-line of the positive lens forming the cemented lens.

In the endoscope objective lens of the invention, it is preferable that the conditional expression (2) below is satisfied, it is more preferable that the conditional expression (2A) below is satisfied, or it is even more preferable that the conditional expression (2B) below is satisfied:

$$-20 < 1/(Pc \times fw) < 0 \tag{2},$$

$$-15 < 1/(Pc \times fw) < -1 \tag{2A) or}$$

$$-10 < 1/(Pc \times fw) < -2 \tag{2B},$$

where Pc is a refractive power of the cemented surface of the cemented lens, and fw is a focal length of the entire system when the focus is set on the farthest object.

In the endoscope objective lens of the invention, it is preferable that the conditional expression (3) below is satisfied, or it is more preferable that the conditional expression (3A) below is satisfied:

$$-5 < fG3/fw < -1.2 \tag{3) or}$$

$$-4 < fG3/fw < -1.5 \tag{3A},$$

where fG3 is a focal length of the third lens group, and fw is a focal length of the entire system when the focus is set on the farthest object.

In the endoscope objective lens of the invention, it is preferable that the conditional expression (4) below is satisfied, it is more preferable that the conditional expression (4A) below is satisfied, or it is even more preferable that the conditional expression (4B) below is satisfied:

$$1.5 < bf/fw < 5.0 \quad (4),$$

$$2.0 < bf/fw < 4.0 \quad (4A) \text{ or}$$

$$2.0 < bf/fw < 3.0 \quad (4B),$$

where bf is a back focus of the entire system in equivalent air distance, and fw is a focal length of the entire system when the focus is set on the farthest object.

In the endoscope objective lens of the invention, it is preferable that the conditional expression (5) below is satisfied, it is more preferable that the conditional expression (5A) below is satisfied, or it is even more preferable that the conditional expression (5B) below is satisfied:

$$1.2 \leq ft/fw \quad (5),$$

$$1.3 \leq ft/fw \quad (5A) \text{ or}$$

$$1.4 \leq ft/fw \quad (5B),$$

where ft is a focal length of the entire system when the focus is set on the nearest object, and fw is a focal length of the entire system when the focus is set on the farthest object.

In the endoscope objective lens of the invention, it is preferable that the first lens group comprises a single lens having a negative refractive power and a cemented lens that is formed by a negative lens and a positive lens cemented together.

In the endoscope objective lens of the invention, it is preferable that the first lens group G1 comprises a cemented lens that is formed by a negative lens and a positive lens cemented together, and the conditional expression (6) below is satisfied, or it is more preferable that the conditional expression (6A) below is satisfied:

$$-20 < f23/fw < 0 \quad (6) \text{ or}$$

$$-15 < f23/fw < -1.5 \quad (6A),$$

where f23 is a focal length of the cemented lens of the most object-side lens group, and fw is a focal length of the entire system when the focus is set on the farthest object.

It should be noted that "the farthest point" as used herein means the farthest point within a distance range on the object side to be observed, and "the nearest point" as used herein means the nearest point within the distance range on the object side to be observed.

It should be noted that the "lens group" as used herein may not necessarily include a plurality of lenses and there may be a lens group including only one lens.

It should be noted that the "single lens" as used herein refers to one lens that is not a cemented lens.

It should be noted that, the sign with respect to the refractive power of any lens or lens group including an aspherical surface, among the above-described lenses or lens groups, is that of the paraxial region.

It should be noted that "substantially" in the expression "... substantially consists (consisting) of four lens groups" is intended to mean that the objective lens of the invention may include, besides the lens groups recited as the constituent elements, lenses substantially without any power, optical elements other than lenses, such as stops and glass covers, and lens flanges, lens barrels, imaging elements, etc.

The endoscope of the invention is provided with the above-described endoscope objective lens of the invention.

The endoscope objective lens of the invention has a four-group configuration with a negative-positive-negative-positive refractive power arrangement, wherein, during focusing from the farthest object to the nearest object, at least two lens groups including the positive second lens group and the negative third lens group are moved, and the configuration of the third lens group is suitably set. Therefore, a magnified observation effect can be obtained, variation of aberration, in particular, variation of chromatic aberration along with movement of the lenses can be reduced, and successful aberration correction can be achieved.

The endoscope of the invention is provided with the endoscope objective lens of the invention. Therefore, a magnified observation effect can be obtained, and there is low variation of aberration, in particular, variation of chromatic aberration during change from a far point side observation state to a near point magnified observation state. Thus, a good observation image can be provided.

DESCRIPTION OF PREFERRED EMBODIMENTS

Figure 1:
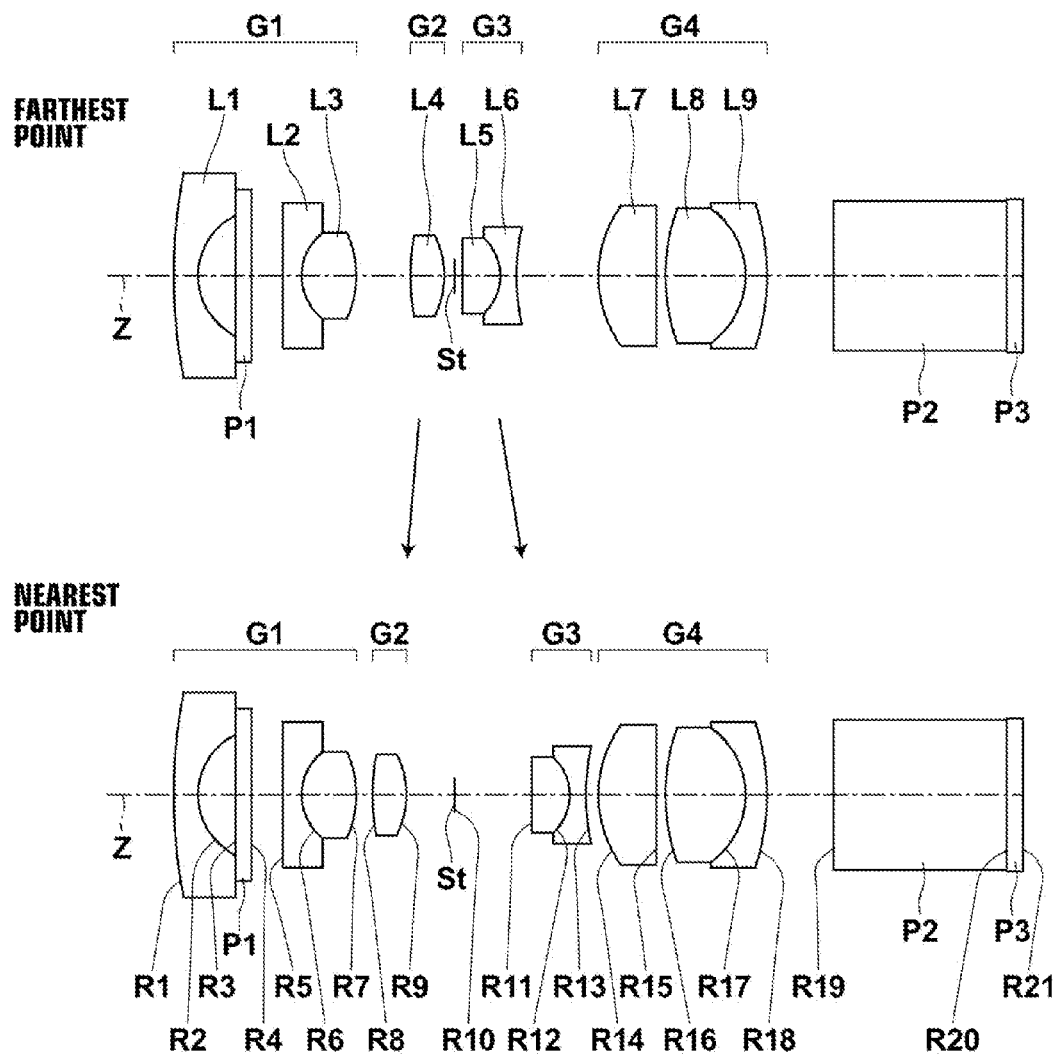
FIG. 1 is a sectional view illustrating the configuration of an endoscope objective lens of Example 1 of the invention.

Hereinafter, an embodiment of the present invention will be described in detail with reference to the drawings. FIG. 1 shows the configuration of an endoscope objective lens according to one embodiment of the invention in a cross section including the optical axis Z. The configuration example shown in FIG. 1 corresponds to the lens configuration of Example 1, which will be described later. In FIG. 1, the left side is the object side, and the right side is the image side.

The endoscope objective lens of this embodiment substantially consists of four lens groups, the four lens groups consisting of a first lens group G1 having a negative refractive power, a second lens group G2 having a positive refractive power, a third lens group G3 having a negative refractive power and a fourth lens group G4 having a positive refractive power, wherein, during focusing from the farthest object to the nearest object, the first lens group G1 is fixed, and the second lens group G2 and the third lens group G3 are moved along the optical axis Z.

The lens configuration when the focus is set on the farthest object (which may hereinafter be referred to as "farthest point observation state") is shown at the upper portion of FIG. 1, and the lens configuration when the focus is set on the nearest object (which may hereinafter be referred to as "nearest point observation state") is shown at the lower portion of FIG. 1.

Also, schematic directions of movement of the second lens group G2 and the third lens group G3 that are moved during the focusing from the farthest point observation state to the nearest point observation state are shown by the arrows in FIG. 1.

In the example shown in FIG. 1, the first lens group G1 includes, in order from the object side, a negative lens L1 and a cemented lens that is formed by a negative lens L2 and a positive lens L3 cemented together. The second lens group G2 includes one positive lens L4. The third lens group G3 includes a cemented lens that is formed by a positive lens L5 and negative lens L6 cemented together in this order from the object side. The fourth lens group G4 includes, in order from the object side, a positive lens L7 and a cemented lens that is formed by a positive lens L8 and a negative lens L9 cemented together.

In the example shown in FIG. 1, an aperture stop St is disposed between the second lens group G2 and the third lens group G3, and an optical member P1 in the form of a plane-parallel plate, which is assumed to be a filter, or the like, is disposed between the lens L1 and the lens L2. On the image side of the fourth lens group G4, optical members P2 and P3 in the form of plane-parallel plates, which are assumed to be an optical path changing prism, a filter, a cover glass, or the like, are disposed. However, the aperture stop St and the optical members P1, P2 and P3 are not essential components of the endoscope objective lens of the invention. Although the position of the image-side surface of the optical member P3 is the same as the position of the image surface of the endoscope objective lens in this example, the position of the image surface is not necessarily limited to the position in this example.

In the endoscope objective lens of this embodiment, the first lens group G1 is fixed during the focusing. This is because that, in the case of endoscopes, the objective lens is often mounted on the endoscope without a protective member and the most object-side lens often serves as an optical window, and in this case, it is impossible to configure such that the most object-side lens is movable, in order to ensure air tightness.

In the endoscope objective lens of the example shown in FIG. 1, the second lens group G2 and the third lens group G3 are moved during the focusing. With the configuration where the negative lens group and the positive lens group are moved, the variation of aberration, in particular, the variation of chromatic aberration along with movement of the lenses can successfully be minimized. Further, in the case where two or more lens groups are moved during focusing, higher freedom of setting a focusing speed relative to a traveling distance of each lens group can be provided, thereby providing more convenience to the user.

It should be noted that a configuration where the fourth lens group G4 is also moved during focusing, in addition to the second lens group G2 and the third lens group G3, is also possible. In this case, higher effects of the above-described minimization of the variation of aberration along with movement of the lenses and of the freedom of setting a focusing speed relative to a traveling distance of each lens group can be obtained.

However, for an endoscope objective lens, for which compactness is strongly desired, simplification of a mechanism for moving the lens groups is also important. For example, as to a four-group configuration having a negative-positive-negative-positive refractive power arrangement in order from the object side, when it is configured such that two lens groups including one positive lens group and one negative lens group are moved during focusing, minimization of the variation of aberration along with movement of the lenses can be achieved and higher freedom of setting a focusing speed relative to a traveling distance of each lens group can be provided while achieving the simplification of the mechanism for moving the lens groups. In this case, as the positive lens group to be moved, it is preferable to select the second lens group G2, which can easily be formed by relatively fewer lenses than the fourth lens group G4, in view of the simplification of the moving mechanism.

The negative lens group of the lens groups to be moved has a large influence on the variation of aberration, in particular, the variation of chromatic aberration along with movement of the lenses. In this embodiment, the configuration of the third lens group G3, which is the negative lens group to be moved, is suitably set. Namely, the third lens group G3 is formed by a cemented lens that is formed by a positive lens and a negative lens cemented together in this order from an object side, wherein the cemented surface of the cemented lens is oriented such that the concave surface faces the object side. By forming the negative lens group to be moved by a cemented lens, the variation of chromatic aberration along with movement of the lenses can be minimized.

Further, in order to provide an endoscope with wide angle of view, the most object-side lens of the entire system is a negative lens having a strong power. Therefore, in the case where a cemented lens is formed using the negative lens included in the negative lens group to be moved, it is advantageous, in view of aberration correction of the entire lens system, to cement the positive lens and the negative lens together in this order from the object side.

Also, in the case where the cemented surface of the cemented lens of the negative lens group to be moved is oriented such that the concave surface faces the object side, aberration correction at the cemented surface having a negative power is effectively achieved while achieving the size reduction, and this is advantageous for aberration correction of the entire lens system.

It is preferable that the endoscope objective lens of this embodiment satisfies one of or any combination of the conditional expressions (1) to (5) below:

$$0 < \nu n - \nu p \quad (1),$$

$$-20 < 1/(Pc \times fw) < 0 \quad (2),$$

$$-5 < fG3/fw < -1.2 \quad (3),$$

$$1.5 < bf/fw < 5.0 \quad (4) \text{ and}$$

$$1.2 \leq ft/fw \quad (5),$$

where vn is an Abbe number with respect to the d-line of the negative lens forming the cemented lens of the third lens group, vp is an Abbe number with respect to the d-line of the positive lens forming the cemented lens of the third lens group, Pc is a refractive power of the cemented surface of the cemented lens of the third lens group, fG3 is a focal length of the third lens group, bf is a back focus of the entire system in equivalent air distance, fw is a focal length of the entire system when the focus is set on the farthest object, and ft is a focal length of the entire system when the focus is set on the nearest object.

The conditional expression (1) relates to dispersive characteristics of a material forming the cemented lens of the third lens group G3. If the lower limit of the conditional expression (1) is not reached, the variation of chromatic aberration along with movement of the lenses is large. When the conditional expression (1) is satisfied, the variation of chromatic aberration along with movement of the lenses can successfully be minimized.

In order to more successfully minimize the variation of chromatic aberration along with movement of the lenses, it is more preferable that the conditional expression (1A) below is satisfied, or it is even more preferable that the conditional expression (1B) below is satisfied:

$$3 < \nu n - \nu p \quad (1A)$$ or $$5 < \nu n - \nu p \quad (1B).$$

The conditional expression (2) relates to the ratio of the power of the third lens group G3 relative to the power of the entire system. If the lower limit of the conditional expression (2) is not reached or the upper limit of the conditional expression (2) is exceeded, the variation of chromatic aberration along with movement of the lenses is large. When the conditional expression (2) is satisfied, the variation of chromatic aberration along with movement of the lenses can successfully be minimized.

In order to more successfully minimize the variation of chromatic aberration along with movement of the lenses, it is more preferable that the conditional expression (2A) below is satisfied, or it is even more preferable that the conditional expression (2B) below is satisfied:

$$-15 < 1/(Pc \times fw) < -1 \quad (2A)$$ or $$-10 < 1/(Pc \times fw) < -2 \quad (2B).$$

The conditional expression (3) relates to the ratio of the power of the third lens group G3 relative to the power of the entire system. If the lower limit of the conditional expression (3) is not reached, the amount of movement of the third lens group G3 is increased, resulting in size increase of the lens system. If the upper limit of the conditional expression (3) is exceeded, it is difficult to achieve successful aberration correction. When the conditional expression (3) is satisfied, successful aberration correction can be achieved while maintaining desired compactness of the endoscope objective lens.

In order to achieve further size reduction and more successful aberration correction, it is more preferable that the conditional expression (3A) below is satisfied:

$$-4 < fG3/fw < -1.5 \quad (3A).$$

The conditional expression (4) relates to the ratio between the back focus and the focal length of the entire system. In an electronic endoscope, which is the main stream in recent years, various filters, such as an optical low-pass filter, an infrared cutoff filter, etc., may be disposed between the endoscope objective lens and the image sensor. In an endoscope of a type where the imaging surface of the image sensor is disposed parallel to the longitudinal direction of the inserted section of the endoscope, as described later, an optical path changing member, such as a prism, for changing the direction of the optical path is typically inserted between the endoscope objective lens and the image sensor, and therefore a sufficient length of back focus is necessary. If the lower limit of the conditional expression (4) is not reached, it is difficult to ensure a sufficient length of back focus for disposing the various filters, the optical path changing member, etc. If the upper limit of the conditional expression (4) is exceeded, the entire length of the optical system is long, resulting in size increase of the optical system. When the conditional expression (4) is satisfied, size increase of the optical system can be prevented while ensuring a sufficiently long back focus.

In order to achieve a longer back focus and further size reduction of the optical system, it is more preferable that the conditional expression (4A) below is satisfied, or it is even more preferable that the conditional expression (4B) below is satisfied:

$$2.0 < bf/fw < 4.0 \quad (4A)$$ or $$2.0 < bf/fw < 3.0 \quad (4B).$$

In the conditional expression (5), ft/fw indicates a magnification. If the lower limit of the conditional expression (5) is not reached, the magnification is too low to obtain a high level of magnified observation effect. When the conditional expression (5) is satisfied, a high level of magnified observation effect can be obtained.

It should be noted that, in order to obtain a higher level of magnified observation effect, it is more preferable that the conditional expression (5A) below is satisfied, or it is even more preferable that the conditional expression (5B) below is satisfied:

$$1.3 \leq ft/fw \quad (5A)$$ or $$1.4 \leq ft/fw \quad (5B).$$

Further, it is preferable that, in the endoscope objective lens of this embodiment, the most object-side first lens group G1 includes a single lens having a negative refractive power, and a cemented lens that is formed by a negative lens and a positive lens cemented together. The reason is as follows. The most object-side lens of an endoscope objective lens often has a strong negative power to provide a wide angle of view, and is therefore preferably formed by a single lens. Further, since there is a lens group that is moved during focusing, it is preferable that each lens group has corrected chromatic aberration. In particular, it is preferable that the first lens group G1, which has high ray height, includes a cemented lens in view of the chromatic aberration correction.

It should be noted that, in the case where the first lens group G1 includes a single lens having a negative refractive power and a cemented lens that is formed by a negative lens and a positive lens cemented together, it is advantageous, in view of wide angle of view, that the most object-side lens group includes, in order from the object side, a negative single lens and a cemented lens that is formed by a negative lens and a positive lens cemented together in this order from the object side, as in the example shown in FIG. 1.

In the case where the first lens group G1 includes a cemented lens that is formed by a negative lens and a positive lens cemented together, it is preferable that the conditional expression (6) below is satisfied:

$$-20 < f23/fw < 0 \quad (6),$$

where f23 is a focal length of the cemented lens of the most object-side lens group, and fw is a focal length of the entire system when the focus is set on the farthest object.

The conditional expression (6) relates to the ratio of the power of the cemented lens of the first lens group G1. If the lower limit of the conditional expression (6) is not reached, it is difficult to achieve successful aberration correction. If the upper limit of the conditional expression (6) is exceeded, it is difficult to ensure a sufficient length of back focus. When the conditional expression (6) is satisfied, successful aberration correction can be achieved while ensuring a sufficient length of back focus.

In order to provide a longer back focus and achieve more successful aberration correction, it is more preferable that the conditional expression (6A) below is satisfied:

$$-15 < f23/fw < -1.5 \quad (6A).$$

It should be noted that, in the case where the endoscope objective lens is mounted on an endoscope without a protective member, the most object-side lens is exposed to body fluids, a cleaning fluid, direct sunlight, fat and oil, etc. Therefore, it is preferable to form this lens by using a material that has high water resistance, high weather resistance, high acid resistance, high chemical resistance, etc. For example, it is preferable to use a material that meets rank 1 of the reduction rate rank of the "water resistance in powder form" and "acid resistance in powder form" standards and rank 1 of the "surface weather resistance" standard established by Japan Optical Glass Manufacturer's Association.

Next, numerical examples of the endoscope objective lens of the invention are described.

Example 1

The lens configuration of the endoscope objective lens of Example 1 is as shown FIG. 1, and the manner of illustration is as described above. Therefore, the same explanations are not repeated here.

The schematic configuration of the endoscope objective lens of Example 1 is as follows. Namely, four lens groups including a first lens group G1 having a negative refractive power, a second lens group G2 having a positive refractive power, a third lens group G3 having a negative refractive power and a fourth lens group G4 having a positive refractive power are arranged in this order from the object side, where the focusing from the farthest object to the nearest object is achieved by moving the second lens group G2 toward the object side along the optical axis Z and moving the third lens group G3 toward the image side along the optical axis Z. An aperture stop St is disposed between the second lens group G2 and the third lens group G3.

The first lens group G1 includes, in order from the object side, a negative lens L1, a negative lens L2 and a positive lens L3. An optical member P1 in the form of a plane-parallel plate, which is assumed to be a filter, or the like, is disposed between the lens L1 and the lens L2. The lens L2 and the lens L3 are cemented together. The second lens group G2 includes one positive lens L4. The third lens group G3 includes, in order from the object side, a positive lens L5 and a negative lens L6. The lens L5 and the lens L6 are cemented together. The fourth lens group G4 includes, in order from the object side, a positive lens L7, a positive lens L8 and a negative lens L9. The lens L8 and the lens L9 are cemented together.

Table 1 shows the detailed configuration of the endoscope objective lens of Example 1. In the table of basic lens data shown at the upper portion of Table 1, each value in the column of "Si" represents the surface number of the i-th (i=1, 2, 3, . . . ) surface, where the surface of the most object-side element is the 1st surface and the number is sequentially increased toward the image side; each value in the column of "Ri" represents the radius of curvature of the i-th surface; each value in the column of "Di" represents the surface interval between the i-th surface and the i+1-th surface along the optical axis Z; each value in the column of "Ndj" represents the refractive index with respect to the d-line (the wavelength of 587.6 nm) of the j-th (j=1, 2, 3, . . . ) element, where the most object-side optical element is the 1st element and the number is sequentially increased toward the image side; and each value in the column of "vdj" represents the Abbe number with respect to the d-line of the j-th element. The sign with respect to the radius of curvature is provided such that a surface shape that is convex toward the object side is positive and a surface shape that is convex toward the image side is negative.

It should be noted that the basic lens data also includes data of the aperture stop St and the optical members P1, P2 and P3. In the column of the surface number, the text "(St)" is shown together with the surface number of the surface corresponding to the aperture stop St. Further, texts "(Variable 1)", "(Variable 2)", "(Variable 3)" and "(Variable 4)" shown respectively in the column on the right side of the column of the interval between the first lens group G1 and the second lens group G2, the interval between the second lens group G2 and the aperture stop St, the interval between the aperture stop St and the third lens group G3, and the interval between the third lens group G3 and the fourth lens group G4, which are changed during focusing.

The table shown at the lower portion of Table 1 shows the object distance, and values of the above-described intervals that are changed during focusing as (Variable 1), (Variable 2), (Variable 3) and (Variable 4) when the focus is set on the farthest object and when the focus is set on the nearest object, respectively.

It should be noted that the numerical values shown in Table 1 are normalized such that the focal length of the entire system when the focus is set on the farthest object is "1". The values shown in Table 1 are rounded at predetermined decimal places.

TABLE 1

Example 1

| Si | Ri | Di | Ndj | vdj |
|---|---|---|---|---|
| 1 | 6.954 | 0.314 | 1.8830 | 40.8 |
| 2 | 0.873 | 0.483 | | |
| 3 | ∞ | 0.210 | 1.6990 | 30.1 |
| 4 | ∞ | 0.402 | | |
| 5 | ∞ | 0.244 | 1.8830 | 40.8 |
| 6 | 0.714 | 0.705 | 1.4388 | 94.9 |
| 7 | −1.328 | 0.698 | (Variable 1) | |
| 8 | 2.835 | 0.440 | 1.4875 | 70.2 |
| 9 | −1.160 | 0.129 | (Variable 2) | |
| 10 (St) | ∞ | 0.105 | (Variable 3) | |
| 11 | ∞ | 0.489 | 1.7283 | 28.5 |
| 12 | −0.666 | 0.210 | 1.8830 | 40.8 |
| 13 | 3.004 | 1.057 | (Variable 4) | |
| 14 | 1.557 | 0.747 | 1.5317 | 48.8 |
| 15 | ∞ | 0.119 | | |
| 16 | 2.582 | 1.034 | 1.4388 | 94.9 |
| 17 | −1.074 | 0.279 | 1.9229 | 18.9 |
| 18 | −2.909 | 0.861 | | |
| 19 | ∞ | 2.235 | 1.5592 | 53.9 |
| 20 | ∞ | 0.210 | 1.5163 | 64.1 |
| 21 | ∞ | | | |

| | Farthest point | Nearest point |
|---|---|---|
| Object distance | 9.43 | 1.29 |
| (Variable 1) | 0.698 | 0.208 |
| (Variable 2) | 0.129 | 0.619 |
| (Variable 3) | 0.105 | 1.002 |
| (Variable 4) | 1.057 | 0.160 |

Figure 5:
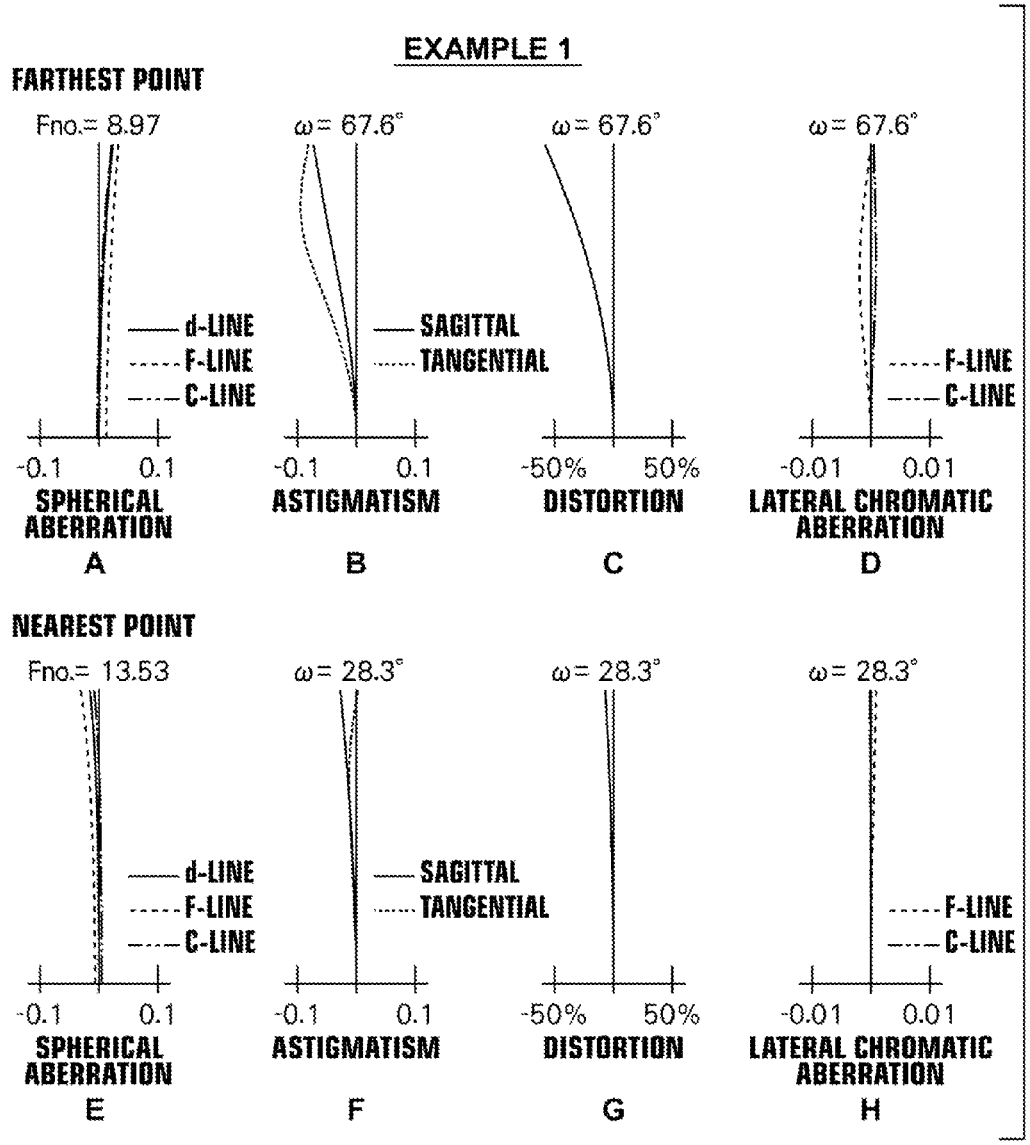
FIG. 5 shows, at "A" to "H", aberration diagrams of the endoscope objective lens of Example 1 of the invention.

FIG. 5 shows, at "A" to "D", aberration diagrams of spherical aberration, astigmatism, distortion and lateral chromatic aberration (chromatic aberration of magnification) in the farthest point observation state of the endoscope objective lens of Example 1. FIG. 5 also shows, at "E" to "H", aberration diagrams of spherical aberration, astigmatism, distortion and lateral chromatic aberration (chromatic aberration of magnification) in the nearest point observation state of the endoscope objective lens of Example 1.

Each of the aberration diagrams of spherical aberration, astigmatism and distortion shows aberration with respect to the d-line serving as the reference wavelength. Each spherical aberration diagram also shows aberration with respect to the C-line (the wavelength of 656.3 nm) and aberration with respect to the F-line (the wavelength of 486.1 nm). Each astigmatism diagram shows aberration in the sagittal direction in the solid line and aberration in the tangential direction in the dashed line. Each lateral chromatic aberration diagram shows aberration with respect to the C-line and aberration with respect to the F-line. The "Fno." shown in the spherical aberration diagrams means the f-number. The symbol "ω" shown in the other aberration diagrams means the half angle of view. The distortion shown is an amount of deviation from an ideal image height, f×tan θ, where f is the focal length of the entire system and θ is the half angle of view (which is handled as a variable, where 0≤θ≤ω).

Values corresponding to the conditional expressions (1) to (6) of the endoscope objective lens of Example 1 are shown in Table 5, which will be shown later, together with those of Examples 2 to 4.

The above-described manners of illustration in the drawings and symbols, meanings and manners of description of the various data of Example 1 apply also to those of Examples 2 to 4, unless otherwise noted, and the same explanations are not repeated in the following description.

Example 2

Figure 2:
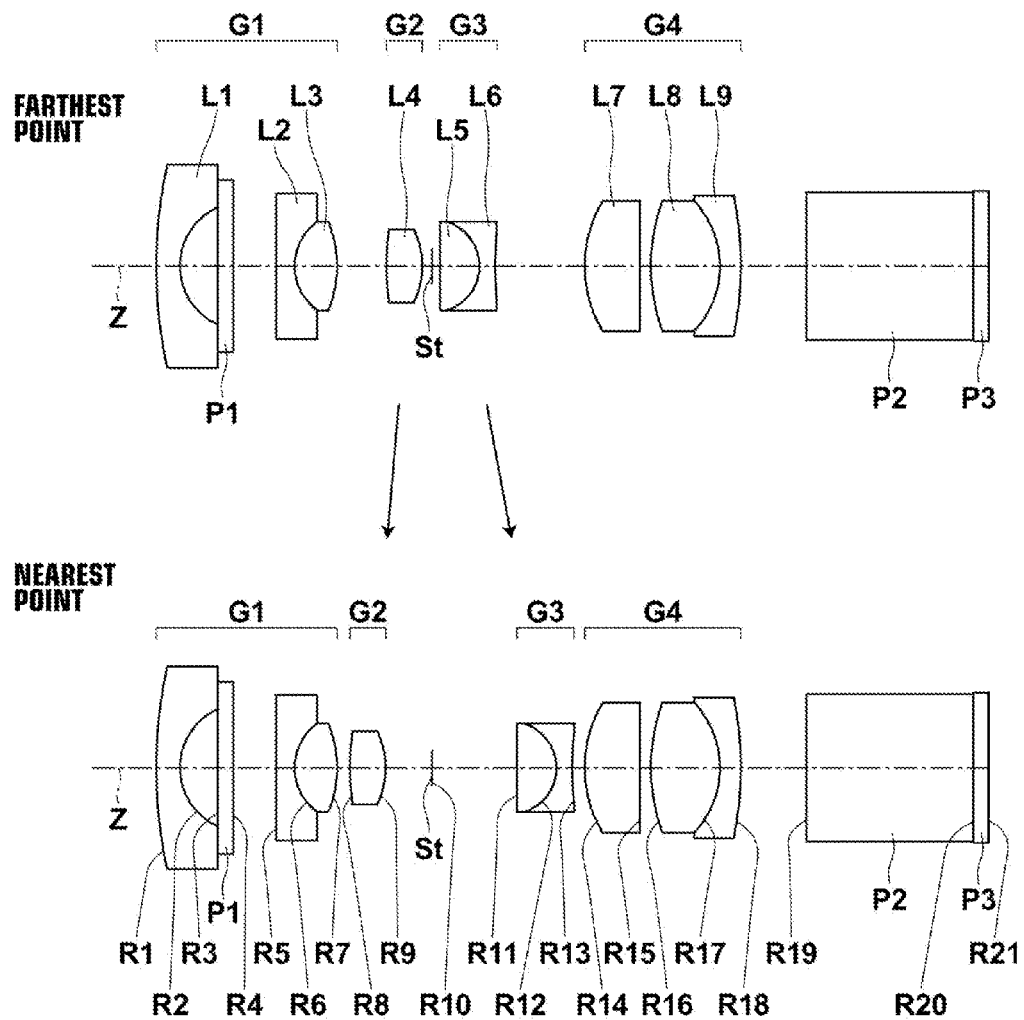
FIG. 2 is a sectional view illustrating the configuration of an endoscope objective lens of Example 2 of the invention.
Figure 6:
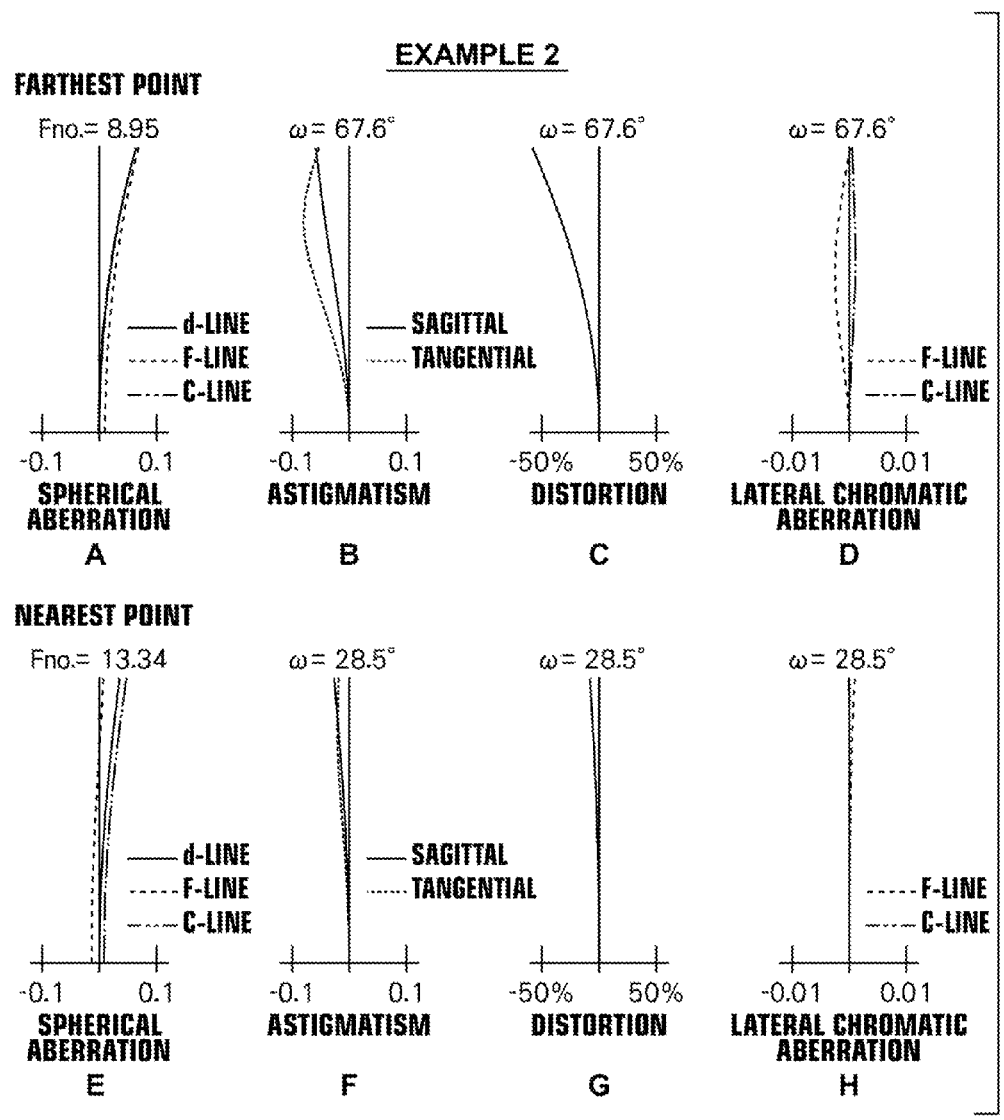
FIG. 6 shows, at "A" to "H", aberration diagrams of the endoscope objective lens of Example 2 of the invention.

FIG. 2 shows the lens configurations in the farthest point observation state and in the nearest point observation state of an endoscope objective lens of Example 2. The schematic configuration of the endoscope objective lens of Example 2 is the same as that of Example 1. Table 2 shows the detailed configuration of the endoscope objective lens of Example 2. FIG. 6 shows, at "A" to "H", aberration diagrams of the endoscope objective lens of Example 2.

TABLE 2

| Example 2 | | | | |
|---|---|---|---|---|
| Si | Ri | Di | Ndj | vdj |
| 1 | 6.341 | 0.314 | 1.8830 | 40.8 |
| 2 | 0.864 | 0.505 | | |
| 3 | ∞ | 0.209 | 1.6990 | 30.1 |
| 4 | ∞ | 0.578 | | |
| 5 | ∞ | 0.244 | 1.9037 | 31.3 |
| 6 | 0.739 | 0.567 | 1.4388 | 94.9 |
| 7 | −1.547 | 0.659 | (Variable 1) | |
| 8 | 3.341 | 0.478 | 1.5481 | 45.8 |
| 9 | −1.127 | 0.129 | (Variable 2) | |
| 10 (St) | ∞ | 0.105 | (Variable 3) | |
| 11 | ∞ | 0.530 | 1.6990 | 30.1 |
| 12 | −0.623 | 0.209 | 1.8830 | 40.8 |
| 13 | 4.895 | 1.199 | (Variable 4) | |
| 14 | 1.699 | 0.735 | 1.4875 | 70.2 |
| 15 | ∞ | 0.149 | | |
| 16 | 2.578 | 0.924 | 1.4875 | 70.2 |
| 17 | −1.280 | 0.279 | 1.9229 | 18.9 |
| 18 | −4.759 | 0.876 | | |
| 19 | ∞ | 2.232 | 1.5592 | 53.9 |
| 20 | ∞ | 0.209 | 1.5163 | 64.1 |
| 21 | ∞ | | | |

| | Farthest point | Nearest point |
|---|---|---|
| Object distance | 9.42 | 1.29 |
| (Variable 1) | 0.659 | 0.170 |
| (Variable 2) | 0.129 | 0.618 |
| (Variable 3) | 0.105 | 1.136 |
| (Variable 4) | 1.199 | 0.167 |

Example 3

Figure 3:
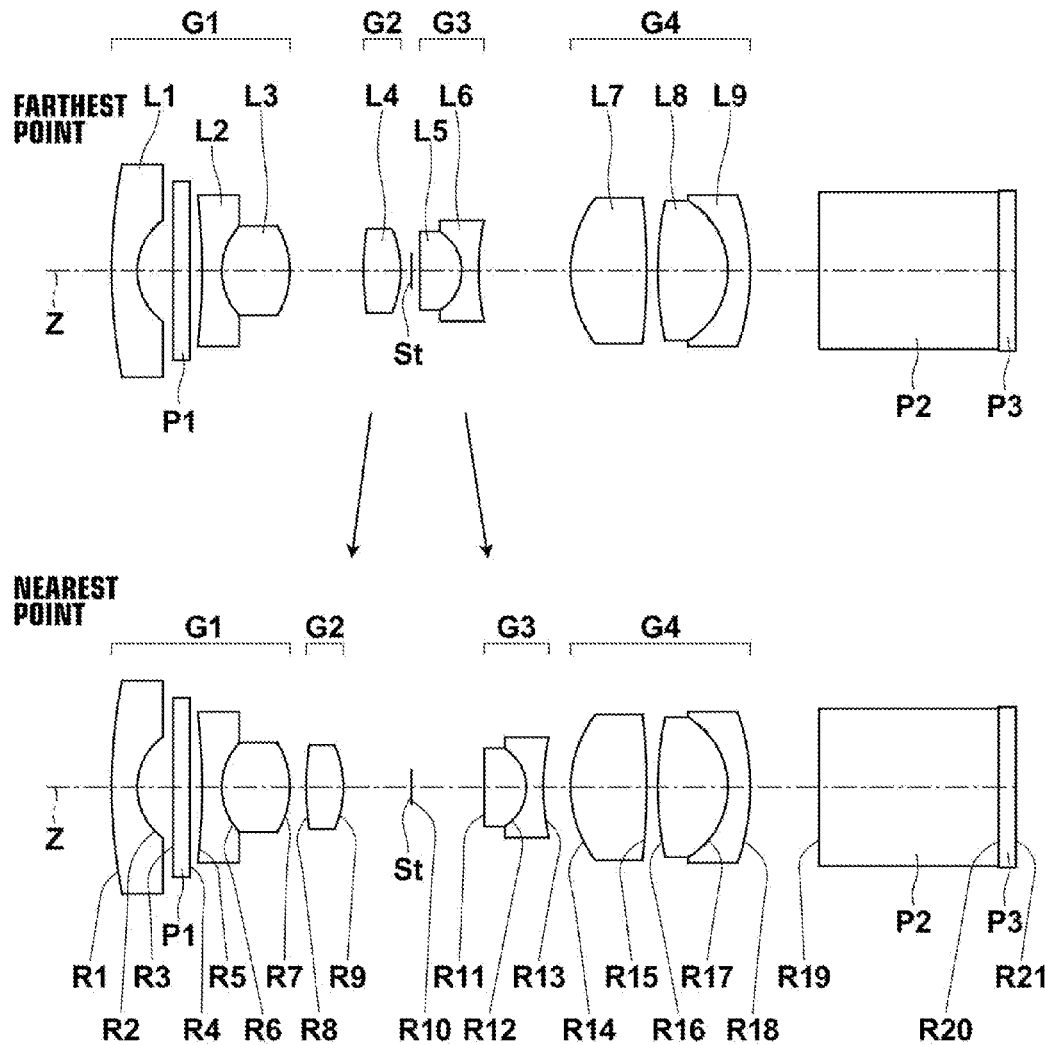
FIG. 3 is a sectional view illustrating the configuration of an endoscope objective lens of Example 3 of the invention.
Figure 7:
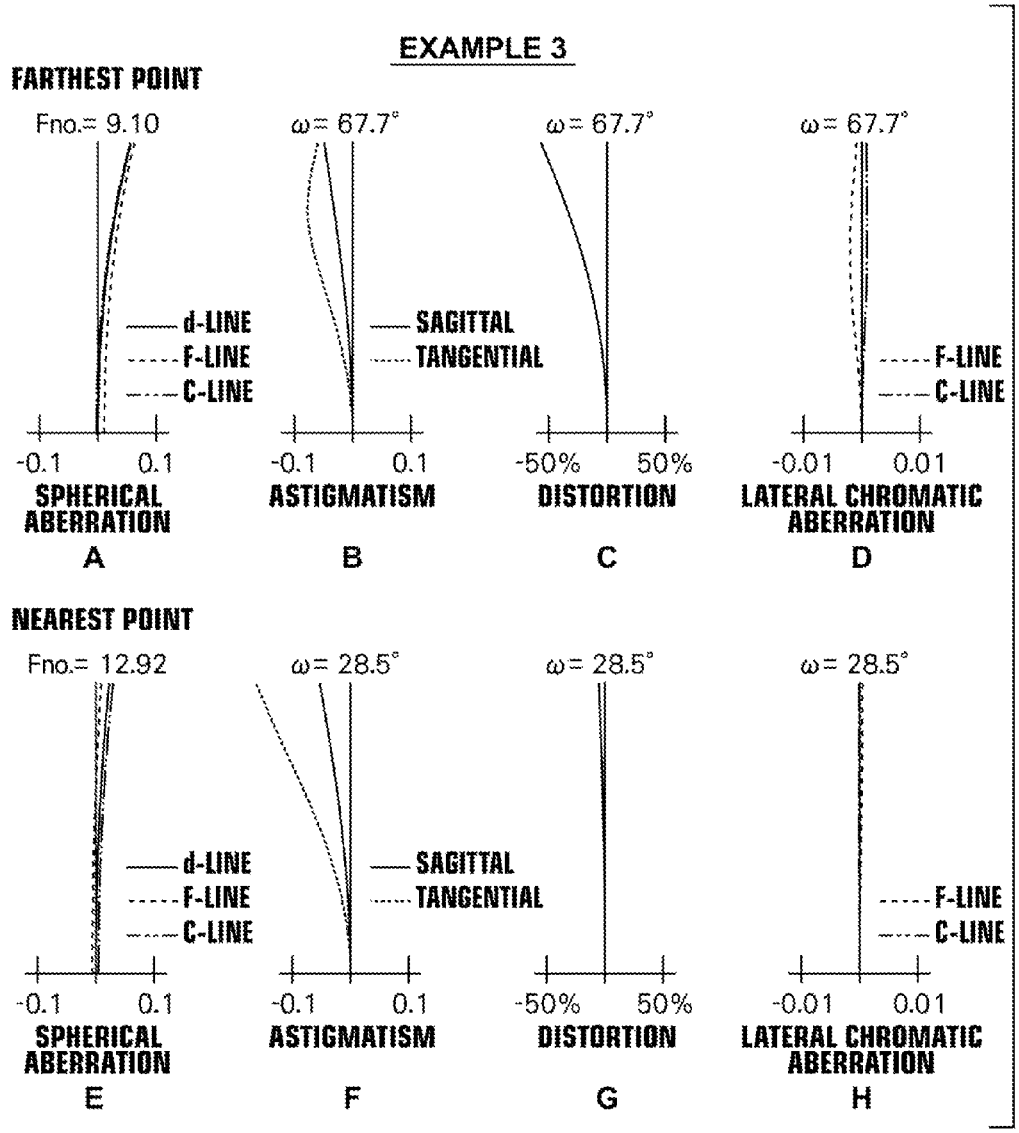
FIG. 7 shows, at "A" to "H", aberration diagrams of the endoscope objective lens of Example 3 of the invention.

FIG. 3 shows the lens configurations in the farthest point observation state and in the nearest point observation state of an endoscope objective lens of Example 3. The schematic configuration of the endoscope objective lens of Example 3 is the same as that of Example 1. Table 3 shows the detailed configuration of the endoscope objective lens of Example 3. FIG. 7 shows, at "A" to "H", aberration diagrams of the endoscope objective lens of Example 3.

TABLE 3

| Example 3 | | | | |
|---|---|---|---|---|
| Si | Ri | Di | Ndj | vdj |
| 1 | 7.285 | 0.328 | 1.8830 | 40.8 |
| 2 | 0.821 | 0.469 | | |
| 3 | ∞ | 0.219 | 1.6889 | 31.1 |
| 4 | ∞ | 0.157 | | |
| 5 | −8.811 | 0.255 | 1.9108 | 35.3 |
| 6 | 0.855 | 0.885 | 1.4388 | 94.9 |
| 7 | −1.102 | 0.957 | (Variable 1) | |
| 8 | 3.929 | 0.483 | 1.4875 | 70.2 |
| 9 | −1.343 | 0.135 | (Variable 2) | |
| 10 (St) | ∞ | 0.109 | (Variable 3) | |
| 11 | ∞ | 0.548 | 1.8052 | 25.4 |
| 12 | −0.602 | 0.219 | 1.9108 | 35.3 |
| 13 | 3.112 | 1.195 | (Variable 4) | |
| 14 | 1.563 | 0.985 | 1.5182 | 58.9 |
| 15 | −8.442 | 0.145 | | |
| 16 | 4.482 | 0.910 | 1.4388 | 94.9 |
| 17 | −1.060 | 0.291 | 1.9229 | 18.9 |
| 18 | −2.966 | 0.892 | | |
| 19 | ∞ | 2.331 | 1.5592 | 53.9 |
| 20 | ∞ | 0.219 | 1.5163 | 64.1 |
| 21 | ∞ | | | |

| | Farthest point | Nearest point |
|---|---|---|
| Object distance | 9.83 | 1.35 |
| (Variable 1) | 0.957 | 0.211 |
| (Variable 2) | 0.135 | 0.880 |
| (Variable 3) | 0.109 | 0.948 |
| (Variable 4) | 1.195 | 0.356 |

Example 4

Figure 4:
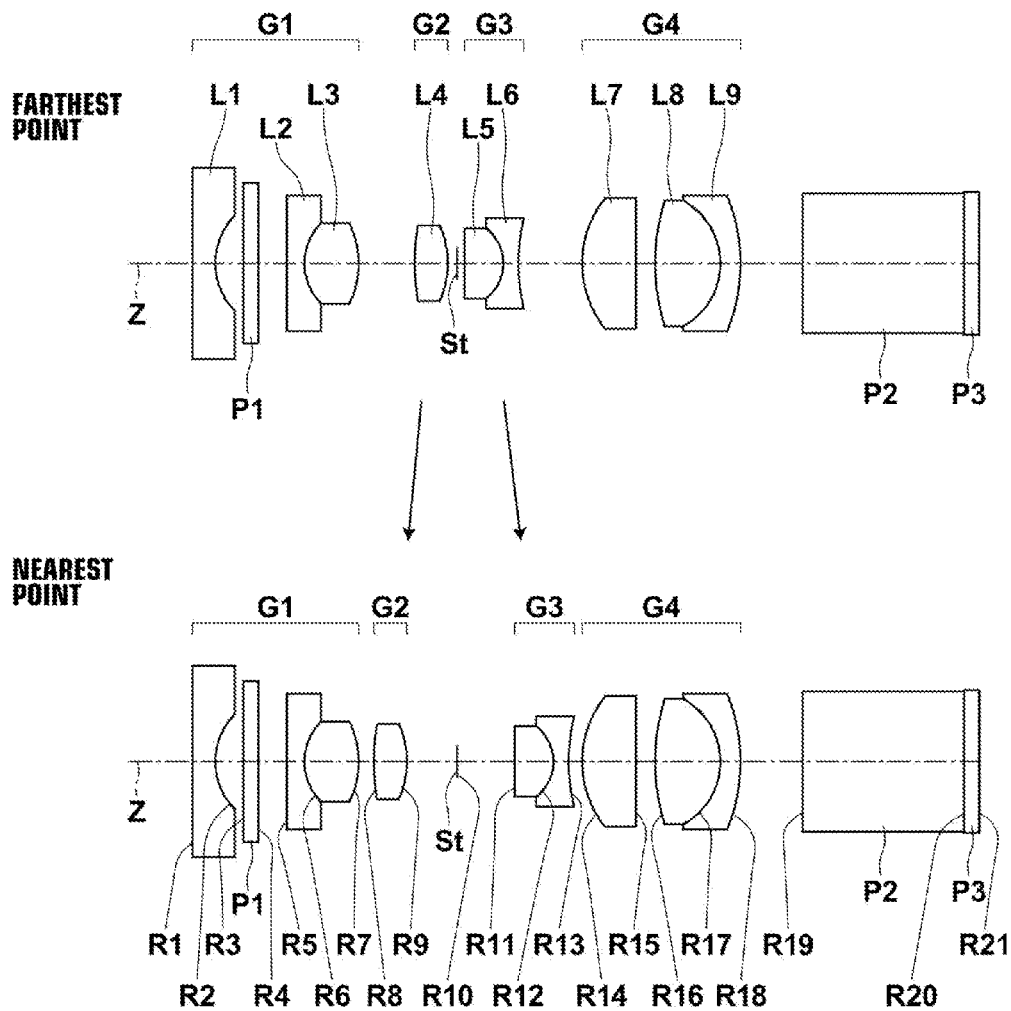
FIG. 4 is a sectional view illustrating the configuration of an endoscope objective lens of Example 4 of the invention.
Figure 8:
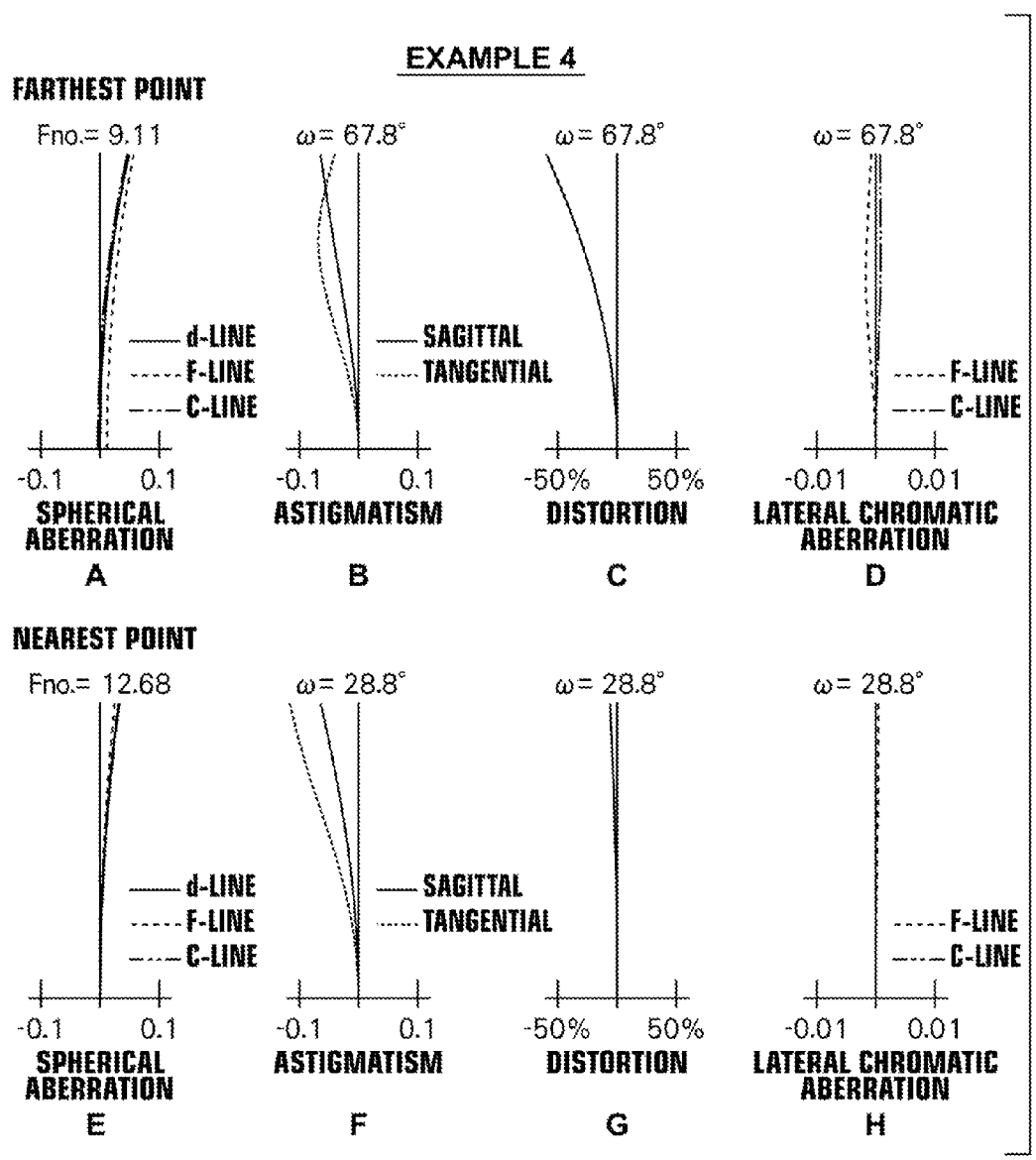
FIG. 8 shows, at "A" to "H", aberration diagrams of the endoscope objective lens of Example 4 of the invention.

FIG. 4 shows the lens configurations in the farthest point observation state and in the nearest point observation state of an endoscope objective lens of Example 4. The schematic configuration of the endoscope objective lens of Example 4 is the same as that of Example 1. Table 4 shows the detailed configuration of the endoscope objective lens of Example 4. FIG. 8 shows, at "A" to "H", aberration diagrams of the endoscope objective lens of Example 4.

TABLE 4

| Example 4 | | | | |
|---|---|---|---|---|
| Si | Ri | Di | Ndj | vdj |
| 1 | ∞ | 0.305 | 1.8830 | 40.8 |
| 2 | 0.915 | 0.378 | | |
| 3 | ∞ | 0.203 | 1.7174 | 29.5 |
| 4 | ∞ | 0.383 | | |
| 5 | ∞ | 0.237 | 1.8830 | 40.8 |
| 6 | 0.776 | 0.733 | 1.4388 | 94.9 |
| 7 | −1.203 | 0.748 | (Variable 1) | |

TABLE 4-continued

Example 4

| | | | | |
|---|---|---|---|---|
| 8 | 2.788 | 0.446 | 1.4970 | 81.5 |
| 9 | −1.256 | 0.125 | (Variable 2) | |
| 10 (St) | ∞ | 0.102 | (Variable 3) | |
| 11 | ∞ | 0.523 | 1.7552 | 27.5 |
| 12 | −0.600 | 0.203 | 1.8830 | 40.8 |
| 13 | 2.604 | 0.857 | (Variable 4) | |
| 14 | 1.413 | 0.722 | 1.5182 | 58.9 |
| 15 | ∞ | 0.257 | | |
| 16 | 2.778 | 0.881 | 1.4388 | 94.9 |
| 17 | −0.968 | 0.271 | 1.9229 | 18.9 |
| 18 | −2.404 | 0.837 | | |
| 19 | ∞ | 2.169 | 1.5592 | 53.9 |
| 20 | ∞ | 0.203 | 1.5163 | 64.1 |
| 21 | ∞ | | | |

| | Farthest point | Nearest point |
|---|---|---|
| Object distance | 10.51 | 1.25 |
| (Variable 1) | 0.748 | 0.199 |
| (Variable 2) | 0.125 | 0.675 |
| (Variable 3) | 0.102 | 0.777 |
| (Variable 4) | 0.857 | 0.181 |

Table 5 shows values corresponding to the conditional expressions (1) to (6) of the above-described Examples 1 to 4. All the Examples 1 to 4 satisfy the conditional expressions (1) to (6). The reference wavelength of the data shown in Table 5 is the d-line.

TABLE 5

| | | Example 1 | Example 2 | Example 3 | Example 4 |
|---|---|---|---|---|---|
| Conditional expression (1) | $\nu n - \nu p$ | 12.3 | 10.6 | 9.8 | 13.3 |
| Conditional expression (2) | $1/(Pc \times fw)$ | −4.30 | −3.39 | −5.70 | −4.69 |
| Conditional expression (3) | fG3/fw | −1.87 | −2.08 | −2.11 | −1.79 |
| Conditional expression (4) | bf/fw | 2.33 | 2.35 | 2.26 | 2.44 |
| Conditional expression (5) | ft/fw | 1.52 | 1.52 | 1.58 | 1.47 |
| Conditional expression (6) | f23/fw | −5.23 | −3.64 | −10.29 | −9.89 |

Figure 9:
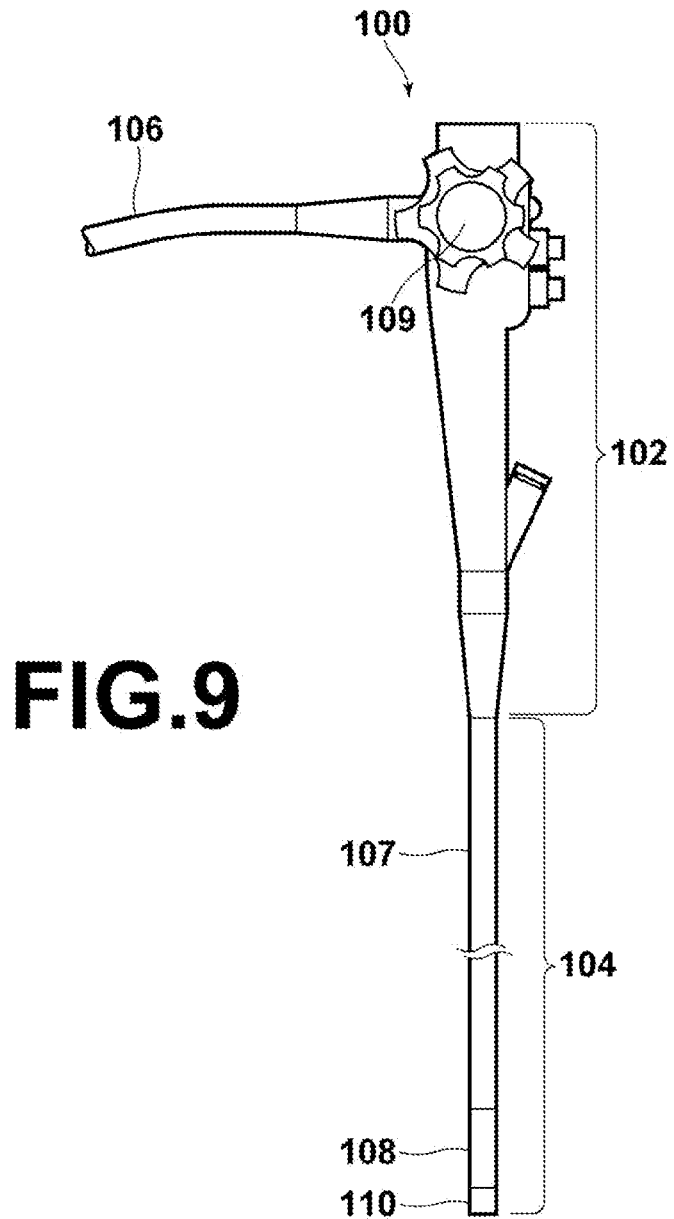
FIG. 9 is a diagram illustrating the schematic configuration of an endoscope according to an embodiment of the invention.

Next, an embodiment of an endoscope to which the endoscope objective lens of the invention is applied is described with reference to FIGS. 9 and 10. An endoscope 100 shown in FIG. 9 primarily includes an operating section 102, an inserted section 104, and a connector section (not shown) from which a universal cord 106 extends. The inserted section 104 to be inserted into the body of a patient is coupled to the distal end side of the operating section 102, and the universal cord 106 for connecting to the connector section for connection to a light source device, or the like, extends from the proximal end side of the operating section 102.

Most part of the inserted section 104 is formed by a soft portion 107, which can bend in any direction along an insertion path. A bending section 108 is coupled to the distal end of the soft portion 107, and a distal end hard portion 110 is coupled to the distal end of the bending section 108. The bending section 108 is provided to orient the distal end hard portion 110 in a desired direction, and a bending operation can be achieved by rotating a bending operation knob 109 provided at the operating section 102.

Figure 10:
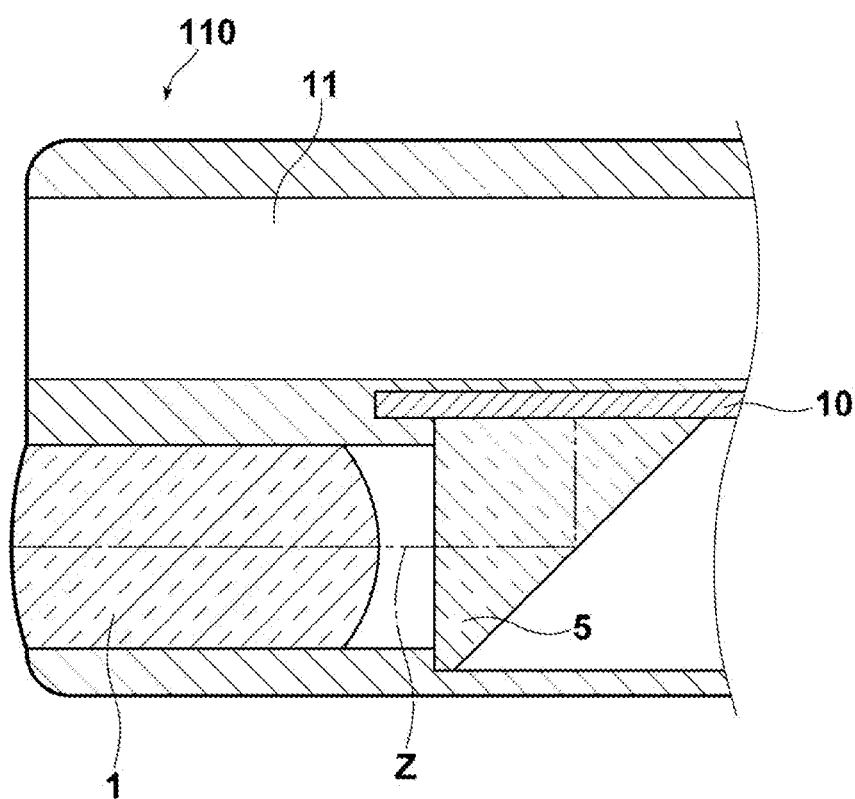
FIG. 10 is a sectional view illustrating the substantial part of a distal end hard portion of the endoscope.

FIG. 10 shows a sectional view of a substantial part of the distal end hard portion 110. As shown in FIG. 10, an endoscope objective lens 1 according to the embodiment of the invention is disposed in the distal end hard portion 110. It should be noted that FIG. 10 conceptually shows the endoscope objective lens 1 in a cross section including the optical axis Z. An optical path changing prism 5 for bending the optical path by 90 degrees is disposed on the image side of the endoscope objective lens 1, and an image sensor 10 is joined onto the image-side surface of the optical path changing prism 5. The image sensor 10 is disposed such that the imaging surface thereof is in the same position as the position of the image surface of the endoscope objective lens 1. The image sensor 10 captures an optical image formed by the endoscope objective lens 1 and outputs an electric signal. The configuration with the bent optical path, as shown in FIG. 10, allows forming a direct view observation optical system at the lower half of the distal end hard portion 110, and forming a surgical tool insertion channel 11 at the upper half of the distal end hard portion 110, and therefore many elements can be placed in the thin inserted section.

The present invention has been described with reference to the embodiments and examples. However, the present invention is not limited to the above-described embodiments and examples, and various modifications may be made to the invention. For example, the values of the radius of curvature, the surface interval, the refractive index, the Abbe number, etc., of each lens component are not limited to the values shown in the above-described numerical examples and may take different values.

For example, although all the endoscope objective lenses of the above-described examples are formed by refractive lenses without using an aspherical surface, the endoscope objective lens of the invention is not limited to the above-described configurations. The endoscope objective lens of the invention may be configured such that the correction of chromatic aberration and other aberrations is achieved using not only spherical refractive lenses but also any of or any combination of aspherical surfaces, GRIN lenses (refractive index-distributed lenses), and diffractive optical elements.

What is claimed is:

1. An endoscope objective lens substantially consisting of four lens groups, the four lens groups consisting of, in order from the object side, a first lens group having a negative refractive power, a second lens group having a positive refractive power, a third lens group having a negative refractive power, and a fourth lens group having a positive refractive power, wherein, during focusing from a farthest object to a nearest object, the first lens group is fixed, and the second lens group and the third lens group are moved along an optical axis, and the third lens group consists of a cemented lens that is formed by a positive lens and a negative lens cemented together in this order from an object side, wherein a cemented surface of the cemented lens is oriented such that a concave surface faces the object side.

2. The endoscope objective lens as claimed in claim 1, wherein the conditional expression (1) below is satisfied:

$$0 < \nu n - \nu p \quad (1),$$

where $\nu n$ is an Abbe number with respect to the d-line of the negative lens forming the cemented lens, and $\nu p$ is an Abbe number with respect to the d-line of the positive lens forming the cemented lens.

3. The endoscope objective lens as claimed in claim 1, wherein the conditional expression (2) below is satisfied:

$$-20 < 1/(Pc \times fw) < 0 \quad (2),$$

where Pc is a refractive power of the cemented surface of the cemented lens, and fw is a focal length of the entire system when the focus is set on the farthest object.

4. The endoscope objective lens as claimed in claim 1, wherein the conditional expression (3) below is satisfied:

$$-5 < fG3/fw < -1.2 \quad (3),$$

where fG3 is a focal length of the third lens group, and fw is a focal length of the entire system when the focus is set on the farthest object.

5. The endoscope objective lens as claimed in claim 1, wherein the conditional expression (4) below is satisfied:

$$1.5 < bf/fw < 5.0 \quad (4),$$

where bf is a back focus of the entire system in equivalent air distance, and fw is a focal length of the entire system when the focus is set on the farthest object.

6. The endoscope objective lens as claimed in claim 1, wherein the conditional expression (5) below is satisfied:

$$1.2 \leq ft/fw \quad (5),$$

where ft is a focal length of the entire system when the focus is set on the nearest object, and fw is a focal length of the entire system when the focus is set on the farthest object.

7. The endoscope objective lens as claimed in claim 1, wherein the first lens group comprises a single lens having a negative refractive power and a cemented lens that is formed by a negative lens and a positive lens cemented together.

8. The endoscope objective lens as claimed in claim 1, wherein the first lens group comprises a cemented lens that is formed by a negative lens and a positive lens cemented together, and
the conditional expression (6) below is satisfied:

$$-20 < f23/fw < 0 \quad (6),$$

where f23 is a focal length of the cemented lens of the first lens group, and fw is a focal length of the entire system when the focus is set on the farthest object.

9. The endoscope objective lens as claimed in claim 1, wherein the conditional expression (1B) below is satisfied:

$$5 < \nu n - \nu p \quad (1B),$$

where $\nu n$ is an Abbe number with respect to the d-line of the negative lens forming the cemented lens, and $\nu p$ is an Abbe number with respect to the d-line of the positive lens forming the cemented lens.

10. The endoscope objective lens as claimed in claim 1, wherein the conditional expression (2B) below is satisfied:

$$-10 < 1/(Pc \times fw) < -2 \quad (2B),$$

where Pc is a refractive power of the cemented surface of the cemented lens, and fw is a focal length of the entire system when the focus is set on the farthest object.

11. The endoscope objective lens as claimed in claim 1, wherein the conditional expression (3A) below is satisfied:

$$-4 < fG3/fw < -1.5 \quad (3A),$$

where fG3 is a focal length of the third lens group, and fw is a focal length of the entire system when the focus is set on the farthest object.

12. The endoscope objective lens as claimed in claim 1, wherein the conditional expression (4B) below is satisfied:

$$2.0 < bf/fw < 3.0 \quad (4B),$$

where bf is a back focus of the entire system in equivalent air distance, and fw is a focal length of the entire system when the focus is set on the farthest object.

13. The endoscope objective lens as claimed in claim 1, wherein the conditional expression (5B) below is satisfied:

$$1.4 \leq ft/fw \quad (5B),$$

where ft is a focal length of the entire system when the focus is set on the nearest object, and fw is a focal length of the entire system when the focus is set on the farthest object.

14. The endoscope objective lens as claimed in claim 1, wherein the first lens group comprises a cemented lens that is formed by a negative lens and a positive lens cemented together, and
the conditional expression (6A) below is satisfied:

$$-15 < f23/fw < -1.5 \quad (6A),$$

where f23 is a focal length the cemented lens of the first lens group, and fw is a focal length of the entire system when the focus is set on the farthest object.

15. An endoscope comprising the endoscope objective lens as claimed in claim 1.

* * * * *